United States Patent [19]
Ohno et al.

[11] Patent Number: 5,276,223
[45] Date of Patent: Jan. 4, 1994

[54] PROCESS FOR PRODUCING 1,1,1,2-TETRAFLUOROETHANE

[75] Inventors: Hiromoto Ohno; Tatsuharu Arai; Kazuo Muramaki; Toshio Ohi; Hidetoshi Nakayama; Yoshitaka Shohji, all of Kanagawa, Japan

[73] Assignee: Showa Denko Kabushiki Kaisha, Tokyo, Japan

[21] Appl. No.: 56,765

[22] Filed: May 4, 1993

[30] Foreign Application Priority Data

Aug. 10, 1992 [JP] Japan .................... 4-213050

[51] Int. Cl.$^5$ .............................. C07C 17/20
[52] U.S. Cl. .................................. 570/164
[58] Field of Search ........................ 570/164

[56] References Cited

U.S. PATENT DOCUMENTS 4,975,156 12/1990 Wismer ............................. 570/164
4,996,378 2/1991 Wright ............................. 570/164

Primary Examiner—Alan Siegel
Attorney, Agent, or Firm—Sughrue, Mion, Zinn, Macpeak & Seas

[57] ABSTRACT

A process for producing 1,1,1,2-tetrafluoroethane through a reaction of trichloroethylene with HF, which comprises the steps of:

(a) allowing trichloroethylene to react with HF in a first reactor to form 1,1,1-trifluoro-2-chloroethane, (b) allowing 1,1,1-trifluoro-2-chloroethane to react with HF in a second reactor to form 1,1,1,2-tetrafluoroethane, (c) introducing the products of the above steps (a) and (b) into a first distillation column where the products are separated into a distillate containing 1,1,1,2-tetrafluoroethane and HCl as main components, a side-cut fraction containing 1,1,1-trifluoro-2-chloroethane and HF as main components and a bottom liquid containing HF as a main component and a small amount of trichloroethylene, and (d) introducing the distillate of the above step (c) into a second distillation column where HCl is recovered as a distillate and a 1,1,1,2-tetrafluoroethane fraction containing small amounts of 1,1,1-trifluoro-2-chloroethane and HF is discharged from the bottom of the second distillation column and introduced into a separately arranged purification step to recover 1,1,1,2-tetrafluoroethane, while the side-cut fraction discharged from the first distillation column is supplemented with HF to adjust the mixing ratio of HF and 1,1,1-trifluoro-2-chloroethane contained therein and recycled into the second reactor and the bottom liquid discharged from the first distillation column is supplemented with trichloroethylene and HF to adjust their mixing ratio and amounts and recycled into the first reactor. The process renders possible simplification of equipments and improvement of energy efficiency in production of 1,1,1,2-tetrafluoroethane.

3 Claims, 2 Drawing Sheets

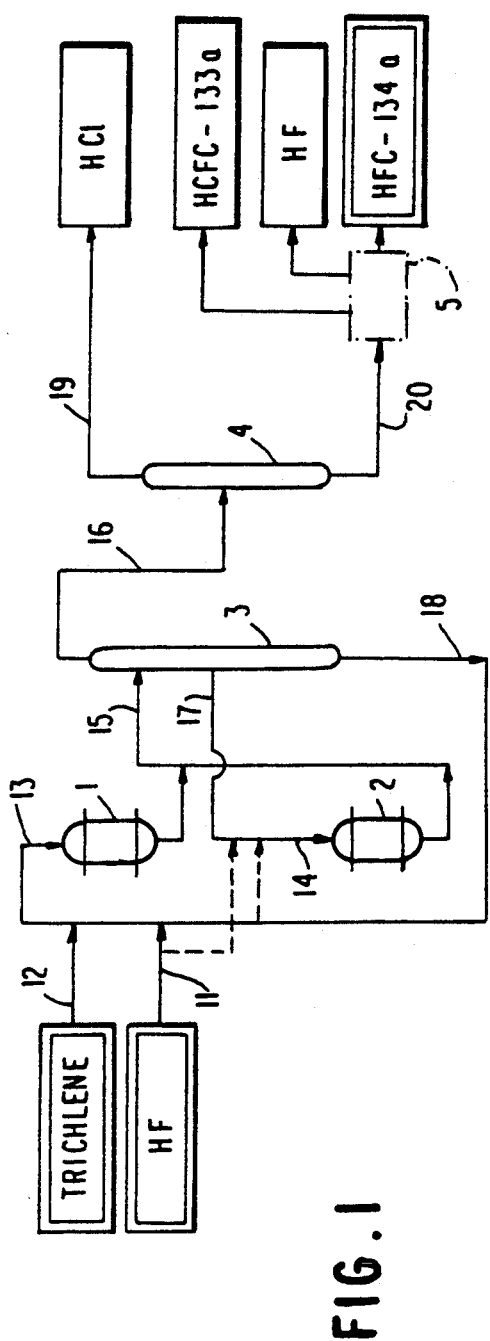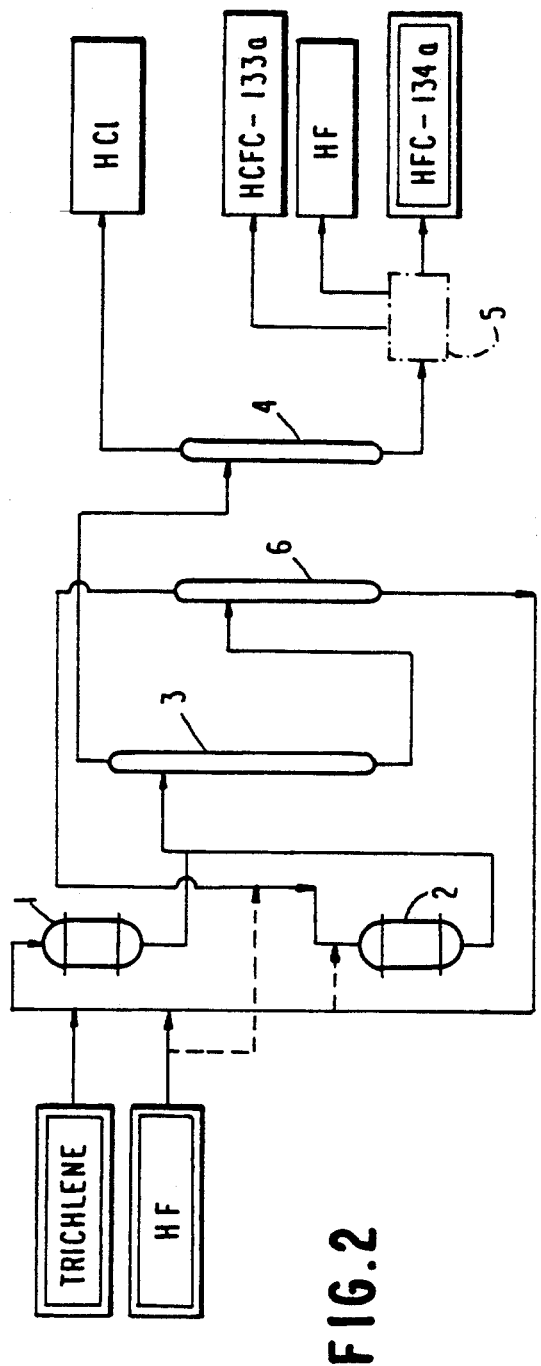

PROCESS FOR PRODUCING 1,1,1,2-TETRAFLUOROETHANE

FIELD OF THE INVENTION

This invention relates to a process for the production of 1,1,1,2-tetrafluoroethane (referred to as "CF$_3$—CH$_2$F" or "HFC-134a" hereinafter) in which HFC-134a is produced efficiently using simple equipments by allowing trichloroethylene (referred to as "CHCl=CCl$_2$" or "trichlene" hereinafter) to react with HF.

BACKGROUND OF THE INVENTION

In general, HFC-134a is produced through the reaction of trichlene with HF. This process is effected not by a single step reaction but by a two step reaction each step having different reaction conditions. That is, trichlene is allowed to react with HF as a first step reaction, thereby forming 1,1,1-trifluoro-2-chloroethane (referred to as "CF$_3$—CH$_2$Cl" or "HCFC-133a" hereinafter), and then the thus formed HCFC-133a is allowed to react with HF as a second step reaction to obtain HFC-134a.

More particularly, a first step reaction represented by the following formula (1) is carried out, for example, under a pressure of 4 kg/cm$^2$G, at a temperature of 250° C. and with an HF/trichlene mol ratio of 6/1.

$$CHCl=CCl_2 + 3\,HF \rightarrow CF_3-CH_2Cl + 2\,HCl \qquad (1)$$

Thereafter, a second step reaction represented by the following formula (2) is carried out, for example, under a pressure of 4 kg/cm$^2$G, at a temperature of 350° C. and with an HF/HCFC-133a mol ratio of 4/1.

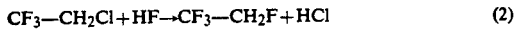

$$CF_3-CH_2Cl + HF \rightarrow CF_3-CH_2F + HCl \qquad (2)$$

In consequence, the prior art HFC-134a production process comprises the steps of carrying out the first step reaction under the above conditions, purifying the product, re-adjusting conditions for the second step reaction, carrying out the second step reaction and then purifying and recovering the thus formed HFC-134a. Since distillation and separation steps are required for each of the reaction steps which are carried out under different reaction conditions, the prior art process has disadvantages in that it requires complex steps and is poor in energy efficiency.

SUMMARY OF THE INVENTION

This invention contemplates overcoming the aforementioned problems involved in the prior art. Accordingly, an object of the present invention is to provide a process for the production of 1,1,1,2-tetrafluoroethane (HFC-134a) from trichloroethylene (trichlene) and HF as starting materials, in which formed products discharged from first and second reactors are combined and subjected to distillation separation using a small number of distillation columns, and the materials to be introduced into each reactor are adjusted by a combination of the thus separated products with the feeding trichlene and HF while separating the concentrated HFC-134a, thus rendering possible simplification of equipments and improvement of energy efficiency.

That is, the first embodiment of the present invention is a process for producing HFC-134a through a reaction of trichloroethylene with HF which comprises the steps of:

(a) allowing trichloroethylene to react with HF in a first reactor to form 1,1,1-trifluoro-2-chloroethane (HCFC-133a), (b) allowing HCFC-133a to react with HF in a second reactor to form HFC-134a, (c) introducing the products of the above steps (a) and (b) into a first distillation column where the products are separated into a distillate containing HFC-134a and HCl as main components, a side-cut fraction containing HCFC-133a and HF as main components and a bottom liquid containing HF as a main component and a small amount of trichloroethylene, and (d) introducing the distillate of the above step (c) into a second distillation column where HCl is recovered as a distillate and an HFC-134a fraction containing small amounts of HCFC-133a and HF is discharged from the bottom and introduced into a separately arranged purification step to recover HFC-134a, while the side-cut fraction discharged from the first distillation column is supplemented with HF to adjust the mixing ratio of HF and HCFC-133a contained therein and recycled into the second reactor and the bottom liquid discharged from the first distillation column is supplemented with trichloroethylene and HF to adjust their mixing ratio and amounts and recycled into the first reactor.

The second embodiment of the present invention is a process for producing HFC-134a through a reaction of trichloroethylene with HF, which comprises the steps of:

(a) allowing trichloroethylene to react with HF in a first reactor to form HCFC-133a, (b) allowing HCFC-133a to react with HF in a second reactor to form HFC-134a, (c) introducing the products of the above steps (a) and (b) into a first distillation column where the products are separated into a distillate containing HFC-134a and HCl as main components and a bottom liquid, and (d) introducing the distillate of the above step (c) into a second distillation column where HCl is recovered as a distillate and a bottom liquid discharged from the second distillation column is introduced into a separately arranged purification step to recover HFC-134a, while the bottom liquid discharged from the first distillation column is introduced into a third distillation column where the resulting distillate is supplemented with HF to adjust the mixing ratio of HF and HCFC-133a contained therein and recycled into the second reactor and a bottom liquid discharged from the third distillation column is supplemented with trichloroethylene and HF to adjust their mixing ratio and amounts and recycled into the first reactor.

The third embodiment of the present invention is a process for producing HFC-134a through a reaction of trichloroethylene with HF, which comprises the steps of:

(a) allowing trichloroethylene to react with HF in a first reactor to form HCFC-133a, (b) allowing HCFC-133a to react with HF in a second reactor to form HFC-134a, (c) introducing the products of the above steps (a) and (b) into a first distillation column where the products are separated into a distillate containing HFC-134a and HCl as main components, a first side-cut fraction containing HCFC-133a and HF as main components, a second side-cut fraction containing trichloroethylene and HF as main components and a bottom liquid containing HF as a main component, and (d) introducing the distillate of the above step (c) into a second distillation column where HCl is recovered as a distillate and an HFC-134a fraction containing small amounts of HCFC-133a and HF is discharged from a bottom of the second distillation column and introduced into a separately arranged purification step to recover HFC-134a, while the first side-cut fraction containing HCFC-133a and HF as main components discharged from the first distillation column is supplemented with HF to adjust the mixing ratio of HF and HCFC-133a contained therein and recycled into the second reactor, the second side-cut fraction containing trichloroethylene and HF as main components discharged from the first distillation column is supplemented with trichloroethylene and HF to adjust their mixing ratio and amounts and recycled into the first reactor and the bottom liquid containing HF as a main component discharged from the first distillation column is recycled into the first and second reactors as a starting material.

BRIEF DESCRIPTION OF THE DRAWINGS

FIG. 1 is a flow sheet showing the first embodiment of the present invention for the production of HFC-134a.

FIG. 2 is a flow sheet showing the second embodiment of the present invention for the production of HFC-134a in which side-cut is not employed.

FIG. 3 is a flow sheet showing the third embodiment of the present invention for the production of HFC-134a.

DETAILED DESCRIPTION OF THE INVENTION

Figure 3:
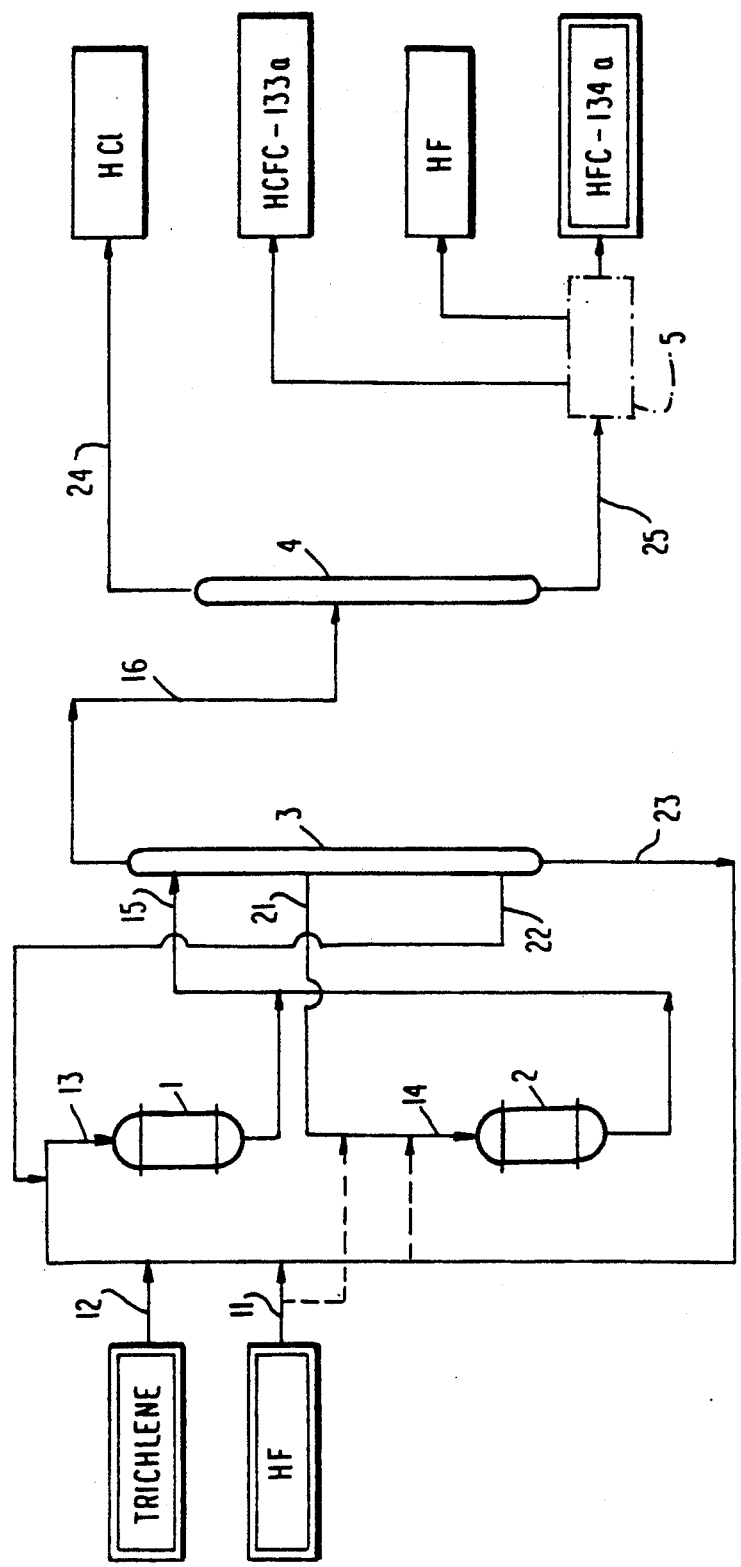

According to the process of the present invention, HCFC-133a is formed by trichlene to react with HF in a first reactor and HFC-134a is formed by allowing HCFC-133a to react with HF in a second reactor. The resulting products from the first and second reactors are introduced into a first distillation column where the products are separated into a distillate containing HFC-134a and HCl as main components, a bottom liquid containing HF as a main component and a small amount of trichlene, and a side-cut fraction containing HCFC-133a and HF as main components. The distillate discharged from the first distillation column is introduced into a second distillation column, where HCl is recovered as a distillate and an HFC-134a fraction containing small amounts of HCFC-133a and HF is discharged from the bottom and introduced into a separately arranged purification step to recover HFC-134a. The bottom liquid discharged from the first distillation column is supplemented with trichlene and HF to adjust their mixing ratio and recycled into the first reactor as a starting material. The side-cut fraction discharged from the first distillation column is supplemented with HF to adjust the mixing ratio of HF and HCFC-133a contained therein and recycled into the second reactor. The term "side-cut fraction" herein used means a fraction discharged from a portion of the first distillation column located above the bottom portion but below the portion at which the products from the first and second reactors are introduced.

In the above instance, the side-cut step may be eliminated by employing a modified process in which the distillate from the first distillation column is introduced into the second distillation column and treated in the same manner, while the bottom liquid discharged from the first distillation column is introduced into a third distillation column, where the resulting distillate is supplemented with HF to adjust the mixing ratio of HF and HCFC-133a contained therein and recycled into the second reactor and the bottom liquid is supplemented with trichlene and HF to adjust their mixing ratio and amounts and recycled into the first reactor.

Alternatively, HCFC-133a is formed by allowing trichlene to react with HF in a first reactor and HFC-134a is formed by allowing HCFC-133a to react with HF in a second reactor. The resulting products from the first and second reactors are introduced into a first distillation column where the products are separated into a distillate containing HFC-134a and HCl as main components, a bottom liquid containing HF as a main component, a first side-cut fraction containing HCFC-133a and HF as main components and a second side-cut fraction containing trichlene and HF as main components. The terms "first side-cut fraction" and "second side-cut fraction" herein used have the same meaning as the side-cut fraction difined above, but the first side-cut fraction is discharged from a portion of the first distillation column located above the portion from which the second side-cut fraction is discharged.

The distillate from the first distillation column is introduced into a second distillation column, where HCl is recovered as a distillate and ah HFC-134a fraction containing small amounts of HCFC-133a and HF is discharged from the bottom and introduced into a separately arranged purification step to recover HFC-134a. The first side-cut fraction containing HCFC-133a and HF as main components discharged from the first distillation column is supplemented with HF to adjust the mixing ratio of HF and HCFC-133a and recycled into the second reactor, the second side-cut fraction containing trichlene and HF as main components is supplemented with trichlene and HF to adjust their mixing ratio and amounts and recycled into the first reactor. The bottom liquid containing HF as a main component discharged from the first distillation column is recycled into the first and second reactors as a starting material.

The embodiments of the present invention are explained in detail below with reference to FIGS. 1, 2 and 3. In these FIGURES, 1 is a first reactor, 2 is a second reactor, 3 is a first distillation column, 4 is a second distillation column, 5 is a purification step, 6 is a third distillation column, 11 is HF to be introduced into the reaction system, 12 is trichlene to be introduced into the reaction system, 13 is a material to be introduced into the first reactor, 14 is a material to be introduced into the second reactor, 15 is combined reaction products, 16 is a distillate from the first distillation column, 17 is a side-cut fraction from the first distillation column, 18 is a bottom liquid from the first distillation column, 19 is a distillate from the second distillation column, 20 is a bottom liquid from the second distillation column, 21 is a first side-cut fraction from the first distillation column, 22 is a second side-cut fraction from the first distillation column, 23 is a bottom liquid from the first distillation column, 24 is a distillate from the second distillation column, and 25 is a bottom liquid from the second distillation column.

FIG. 1 is a flow sheet showing the first embodiment of the present invention. The reaction in first reactor 1 may be carried out under a pressure of from 0 to 6 kg/cm$^2$G, preferably from 0 to 4 kg/cm$^2$G, at a temperature of from 200° to 350° C., preferably from 250° to 300° C. with the HF/trichlene mol ratio of from 4/1 to 20/1, preferably from 6/1 to 10/1, for example, under a pressure of 4 kg/cm$^2$G, at a temperature of 250° C. and with an HF/trichlene mol ratio of 6/1. The reaction in second reactor 2 may be carried out under a pressure of from 0 to 6 kg/cm$^2$G, preferably from 0 to 4 kg/cm$^2$G, at a temperature of from 300° to 380° C., preferably from 300° to 360° C. with the HF/HCFC-133a mol ratio of from 2/1 to 10/1, preferably from 4/1 to 8/1, for example, under a pressure of 4 kg/cm$^2$G, at a temperature of 350° C. and with an HF/HCFC-133a mol ratio of 4/1.

Reaction products discharged from first and second reactors 1 and 2 are combined and introduced into first distillation column 3 as a combined reaction products 15. In this embodiment, combined reaction products 15 are separated into distillate 16, side-cut fraction 17 and bottom liquid 18 in first distillation column 3.

Distillate 16 which contains HCl and HFC-134a as main components is introduced into second distillation column 4 where distillate 16 is separated into distillate 19 and bottom liquid 20. Distillate 19 discharged from second distillation column 4 contains mainly HCl which will be used for other purposes after purification. Bottom liquid 20 which contains HFC-134a as a main component together with small amounts of HF and HCFC-133a is introduced into separately arranged purification step 5 from which HFC-134a is recovered. HF and HCFC-133a contained in bottom liquid 20 are separated in purification step 5 and optionally used as material 13 or 14 of the first or second reactor.

Side-cut fraction 17 discharged from first distillation column 3, which contains HF and HCFC-133a as main components, is supplemented with HF to adjust the mixing ratio of HF and HCFC-133a and recycled into second reactor 2 as material 14.

Bottom liquid 18 discharged from first distillation column 3 contains HF as a main component together with a small amount of trichlene. Though a portion of bottom liquid 18 may be used for the adjustment of the material of second reactor 2, most of bottom liquid 18 is supplemented with fresh HF and trichlene and their concentrations and amounts are adjusted to be used as material 13 of first reactor 1. In FIG. 1, 11 is HF and 12 is trichlene both to be introduced into the reaction system.

In summary, reaction products formed in first and second reactors 1 and 2 are combined and treated in two distillation columns, namely first and second distillation columns 3 and 4, where the reaction products are separated into HFC-134a as the product of interest, HCl as a by-product, an HF fraction containing a small amount of trichlene which can be used for the adjustment of the starting materials and a side-cut fraction that can be used as the material of the second reactor. These fractions are recycled into the reaction and distillation/separation steps in combination with fresh trichlene and HF as supplementary materials. Since the equipments of the first embodiment of the present invention are arranged in the above order, HFC-134a can be produced efficiently using a small number of equipments.

FIG. 2 is a flow sheet showing the second embodiment of the present invention. In this embodiment a side-cut step is not employed, and a bottom liquid from first distillation column 3 is introduced into third distillation column 6, where a distillate which corresponds to the side-cut fraction of the first embodiment is discharged from the top of column 6 and a liquid containing HF as a main component and a small amount of trichlene is discharged from the bottom. In this case, three distillation columns are required because of the use of third distillation column 6, but stability of the operation is improved because of the elimination of the side-cut step.

FIG. 3 is a flow sheet showing the third embodiment of the present invention, in which preferred reaction conditions are the same as those described in the first embodiment. In the third embodiment of the present invention, combined reaction products 15 are separated into distillate 16, first side-cut fraction 21, second side-cut fraction 22 and bottom liquid 23 in first distillation column 3.

Distillate 16 which contains HCl and HFC-134a as main components is introduced into second distillation column 4 where distillate 16 is separated into distillate 24 and bottom liquid 25. Distillate 24 discharged from second distillation column 4 contains mainly HCl which will be used for other purposes after purification. Bottom liquid 25 which contains HFC-134a as a main component together with small amounts of HF and HCFC-133a is introduced into separately arranged purification step 5 from which HFC-134a is recovered. HF and HCFC-133a contained in bottom liquid 25 are separated in purification step 5 and optionally used as material 13 or 14 of the first or second reactor.

First side-cut fraction 21 discharged from first distillation column 3, which contains HF and HCFC-133a as main components, is supplemented with HF to adjust the mixing ratio of HF and HCFC-133a and recycled into second reactor 2 as material 14.

Second side-cut fraction 22 discharged from first distillation column 3, which contains HF and trichlene as main components, is supplemented with fresh HF and trichlene to adjust their concentrations and amounts and recycled into first reactor 1 as material 13.

Bottom liquid 23 discharged from first distillation column 3 contains HF as a main component. Though a portion of bottom liquid 23 may be used for the adjustment of the material of second reactor 2, most of bottom liquid 23 is used as material 13 of first reactor 1. In FIG. 3, 11 is HF and 12 is trichlene both to be introduced into the reaction system.

In summary, reaction products formed in first and second reactors 1 and 2 are combined and treated in two distillation columns, namely first and second distillation columns 3 and 4, where the reaction products are separated into HFC-134a as the product of interest, HCl as a by-product, an HF fraction which can be used for the adjustment of the starting material, a second side-cut fraction containing HF and trichlene that can be used as material 13 to be recycled to first reactor 1 and a first side-cut fraction containing HCFC-133a and HF useful as material 14 to be recycled to second reactor 2. These fractions are recycled into the reaction and distillation/separation steps in combination with fresh trichlene and HF as supplementary materials. Since the equipments of the third embodiment of the present invention are arranged in the above order, HFC-134a can be produced efficiently using a small number of equipments.

Next, the process of the present invention is described in more detail with reference to the following examples. It is to be understood, however, that the examples are for purpose of illustration only and are not intended as a definition of the limits of the present invention.

EXAMPLE 1

A test run was carried out in accordance with the flow sheet shown in FIG. 1, with the results shown in Table 1. In the table, components in each process step are indicated by weight percent, and the flow rate in each step is shown as a relative value in which the flow rate of combined reaction products 15 to be introduced into the first distillation column is taken as 100.

TABLE 1

| Component | 11 | 12 | 13 | 14 | 15 | 16 | 17 | 18 | 19 | 20 |
|---|---|---|---|---|---|---|---|---|---|---|
| [Flow Rate]*1: | | | | | | | | | | |
| HFC-134a | — | — | — | — | 8.8 | 8.8 | — | — | — | 8.8 |
| HCFC-133a | — | — | — | 44.1 | 44.8 | 0.8 | 44.0 | — | — | 0.8 |
| HF | 7.2 | — | 11.1 | 29.7 | 33.8 | 0.2 | 7.5 | 26.1 | — | 0.2 |
| HCl | — | — | — | — | 8.7 | 8.7 | — | — | 8.7 | — |
| Trichlene | — | 11.6 | 12.2 | 0.8 | 1.4 | — | — | 1.4 | — | — |
| Others | — | — | 0.2 | 1.8 | 2.5 | 0.5 | 0.9 | 1.1 | — | 0.5 |
| Total | 7.2 | 11.6 | 23.5 | 76.4 | 100 | 19.0 | 52.4 | 28.6 | 8.7 | 10.3 |
| [Mixing ratio]*2: | | | | | | | | | | |
| HFC-134a | — | — | — | — | 8.8 | 46.32 | — | — | — | 85.44 |
| HCFC-133a | — | — | — | 57.72 | 44.8 | 4.21 | 83.97 | — | — | 7.77 |
| HF | 100 | — | 47.23 | 38.87 | 33.8 | 1.05 | 14.31 | 91.26 | — | 1.94 |
| HCl | — | — | — | — | 8.7 | 45.79 | — | — | 100 | — |
| Trichlene | — | 100 | 51.92 | 1.05 | 1.4 | — | — | 4.9 | — | — |
| Others | — | — | 0.85 | 2.36 | 2.5 | 2.63 | 1.72 | 3.84 | — | 4.85 |
| Total | 100 | 100 | 100 | 100 | 100 | 100 | 100 | 100 | 100 | 100 |

[Note]
*1Flow rate of combined reaction product 15 = 100 kg/hr
*2% by weight

EXAMPLE 3

A test run was carried out in accordance with the flow sheet shown in FIG. 3, with the results shown in Table 2. In the table, components in each process step are indicated by weight percent, and the flow rate in each step is shown as a relative value in which the flow rate of combined reaction products 15 to be introduced into the first distillation column is taken as 100.

TABLE 2

| Component | 11 | 12 | 13 | 14 | 15 | 16 | 21 | 22 | 23 | 24 | 25 |
|---|---|---|---|---|---|---|---|---|---|---|---|
| [Flow Rate]*1: | | | | | | | | | | | |
| HFC-134a | — | — | — | — | 8.8 | 8.8 | — | — | — | — | 8.8 |
| HCFC-133a | — | — | — | 44.1 | 44.8 | 0.8 | 44.0 | — | — | — | 0.8 |
| HF | 7.2 | — | 11.1 | 29.7 | 33.8 | 0.2 | 7.5 | 2.0 | 24.1 | — | 0.2 |
| HCl | — | — | — | — | 8.7 | 8.7 | — | — | — | 8.7 | — |
| Trichlene | — | 11.6 | 12.2 | 1.8 | 0.6 | — | — | 0.6 | — | — | — |
| Others | — | — | 0.2 | — | 2.5 | 0.5 | 0.9 | 0.1 | 1.0 | — | 0.5 |
| Total | 7.2 | 11.6 | 23.5 | 75.6 | 99.2 | 19.0 | 52.4 | 2.7 | 25.1 | 8.7 | 10.3 |
| [Mixing ratio]*2: | | | | | | | | | | | |
| HFC-134a | — | — | — | — | 8.8 | 46.32 | — | — | — | — | 85.44 |
| HCFC-133a | — | — | — | 57.72 | 44.8 | 4.21 | 83.97 | — | — | — | 7.77 |
| HF | 100 | — | 47.23 | 38.87 | 33.8 | 1.05 | 14.31 | 74.07 | 96.02 | — | 1.94 |
| HCl | — | — | — | — | 8.7 | 45.79 | — | — | — | 100 | — |
| Trichlene | — | 100 | 51.92 | 1.05 | 1.4 | — | — | 22.22 | — | — | — |
| Others | — | — | 0.85 | 2.36 | 2.5 | 2.63 | 1.72 | 3.71 | 3.98 | — | 4.85 |
| Total | 100 | 100 | 100 | 100 | 100 | 100 | 100 | 100 | 100 | 100 | 100 |

[Note]
*1, *2: See Table 1.

EXAMPLE 2

A test run was carried out in accordance with the flow sheet shown in FIG. 2. Since this was the same run of Example 1 except that the side-cut step was eliminated, flow rates at respective steps are not shown herein. HFC-134a similar to the case of bottom liquid 20 shown in Table 1 was obtained.

As is evident from the results shown in Table 1, combined reaction products are separated by the two distillation columns and the materials for the first and second reactors are adjusted with the separated fractions in combination with supplementary trichlene and HF, while the by-product HCl is recovered and the HFC-134a product of interest is concentrated.

As is evident from the results shown in Table 2, combined reaction products are separated by the two distillation columns and the materials for the first and second reactors are adjusted with the separated fractions in combination with supplementary trichlene and HF, while the by-product HCl is recovered and the HFC-134a product of interest is concentrated.

As has been described in the foregoing, in the HFC-134a production process of the present invention, reaction products from the first and second reactors are combined prior to their separation by distillation, and the materials for the reactors are adjusted with the separated fractions in combination with supplementary trichlene and HF, while, in the prior art process, the reaction products from the first reactor and those from the second reactor are separated by independent distillation means prior to the adjustment of the materials for the reactors with the separated fractions in combination with supplementary trichlene and HF. Because of this, the inventive process has advantages in that the distillation step is simplified and the energy cost is reduced.

While the invention has been described in detail and with reference to specific embodiments thereof, it will be apparent to one skilled in the art that various changes and modifications can be made therein without departing from the spirit and scope thereof.

What is claimed is:

1. A process for producing 1,1,1,2-tetrafluoroethane through a reaction of trichloroethylene with HF, which comprises the steps of:

(a) allowing trichloroethylene to react with HF in a first reactor to form 1,1,1-trifluoro-2-chloroethane, (b) allowing 1,1,1-trifluoro-2-chloroethane to react with HF in a second reactor to form 1,1,1,2-tetrafluoroethane, (c) introducing the products of the above steps (a) and (b) into a first distillation column where the products are separated into a distillate containing 1,1,1,2-tetrafluoroethane and HCl as main components, a side-cut fraction containing 1,1,1-trifluoro-2-chloroethane and HF as main components and a bottom liquid containing HF as a main component and a small amount of trichloroethylene, and (d) introducing the distillate of the above step (c) into a second distillation column where HCl is recovered as a distillate and a 1,1,1,2-tetrafluoroethane fraction containing small amounts of 1,1,1-trifluoro-2-chloroethane and HF is discharged from the bottom of the second distillation column and introduced into a separately arranged purification step to recover 1,1,1,2-tetrafluoroethane, while the side-cut fraction discharged from the first distillation column is supplemented with HF to adjust the mixing ratio of HF and 1,1,1-trifluoro-2-chloroethane contained therein and recycled into the second reactor and the bottom liquid discharged from the first distillation column is supplemented with trichloroethylene and HF to adjust their mixing ratio and amounts and recycled into the first reactor.

2. A process for producing 1,1,1,2-tetrafluoroethane through a reaction of trichloroethylene with HF, which comprises the steps of:

(a) allowing trichloroethylene to react with HF in a first reactor to form 1,1,1-trifluoro-2-chloroethane, (b) allowing 1,1,1-trifluoro-2-chloroethane to react with HF in a second reactor to form 1,1,1,2-tetrafluoroethane, (c) introducing the products of the above steps (a) and (b) into a first distillation column where the products are separated into a distillate containing 1,1,1,2-tetrafluoroethane and HCl as the main components and a bottom liquid, and (d) introducing the distillate of the above step (c) into a second distillation column where HCl is recovered as a distillate and a bottom liquid from the second distillation column is introduced into a separately arranged purification step to recover 1,1,1,2-tetrafluoroethane, while the bottom liquid discharged from the first distillation column is introduced into a third distillation column where the resulting distillate is supplemented with HF to adjust the mixing ratio of HF and 1,1,1-trifluoro-2-chloroethane contained therein and recycled into the second reactor and the bottom liquid from the third distillation column is supplemented with trichloroethylene and HF to adjust their mixing ratio and amounts and recycled into the first reactor.

3. A process for producing 1,1,1,2-tetrafluoroethane through a reaction of trichloroethylene with HF, which comprises the steps of:

(a) allowing trichloroethylene to react with HF in a first reactor to form 1,1,1-trifluoro-2-chloroethane, (b) allowing 1,1,1-trifluoro-2-chloroethane to react with HF in a second reactor to form 1,1,1,2-tetrafluoroethane, (c) introducing the products of the above steps (a) and (b) into a first distillation column where the products are separated into a distillate containing 1,1,1,2-tetrafluoroethane and HCl as main components, a first side-cut fraction containing 1,1,1-trifluoro-2-chloroethane and HF as main components, a second side-cut fraction containing trichloroethylene and HF as main components and a bottom liquid containing HF as a main component, and (d) introducing the distillate of the above step (c) into a second distillation column where HCl is recovered as a distillate and a 1,1,1,2-tetrafluoroethane fraction containing small amounts of 1,1,1-trifluoro-2-chloroethane and HF is discharged from the bottom of the second distillation column and introduced into a separately arranged purification step to recover 1,1,1,2-tetrafluoroethane, while the first side-cut fraction containing 1,1,1-trifluoro-2-chloroethane and HF as main components discharged from the first distillation column is supplemented with HF to adjust the mixing ratio of HF and 1,1,1-trifluoro-2-chloroethane contained therein and recycled into the second reactor, the second side-cut fraction containing trichloroethylene and HF as main components discharged from the first distillation column is supplemented with trichloroethylene and HF to adjust their mixing ratio and amounts and recycled into the first reactor and the bottom liquid containing HF as a main component discharged from the first distillation column is recycled into the first and second reactors as a starting material.

* * * * *